United States Patent [19]

Shoji et al.

[11] 4,256,961
[45] Mar. 17, 1981

[54] X-RAY SPECTROSCOPE

[75] Inventors: Takashi Shoji, Settsu; Tadashi Utaka, Takatsuki, both of Japan

[73] Assignee: Rigaku Industrial Corporation, Takatsuki, Japan

[21] Appl. No.: 52,942

[22] Filed: Jun. 27, 1979

[51] Int. Cl.³ .......................................... G01N 23/20
[52] U.S. Cl. .................................... 250/272; 250/276
[58] Field of Search ............... 250/272, 273, 276, 274, 250/275

[56] References Cited

U.S. PATENT DOCUMENTS 3,160,747  12/1964  De Vries .............................. 250/276
3,160,749  12/1964  Spielberg ............................ 250/276

Primary Examiner—Craig E. Church
Attorney, Agent, or Firm—A. W. Breiner

[57] ABSTRACT

An X-ray spectroscope comprising a soller slit consisting of a number of parallel plates and disposed such that one end thereof faces an X-ray emitting portion of a sample to be analyzed and a plurality of analysing crystals or total reflection mirrors disposed parallel to one another and spaced apart from one another at a suitable interval. The analysing crystals or total reflection mirrors are orientated with their one ends directed to the other end of the soller slit and such that X-rays having passed through the soller slit are incident on them with a desired angle of incidence.

Also, these analysing crystals or total reflection mirrors each have a convex back side defined by inclined surfaces respectively parallel with incident and reflected X-rays and facing the reflecting surface of the next adjacent analysing crystal or total reflection mirror.

With this X-ray spectroscope it is possible to make effective use of X-rays and prevent divergence in directions normal to the diffracting surface, thus permitting analysis with high efficiency.

10 Claims, 2 Drawing Figures

X-RAY SPECTROSCOPE

BACKGROUND OF THE INVENTION

1. Field of the Invention

This invention relates to X-ray spectroscopes incorporating analysing crystals and total reflection mirrors and used for fluorescent X-ray analyzing method or the like.

2. Description of the Prior Art

Fluorescent X-ray analysers usually incorporate analysing crystals for separating the characteristic X-rays of a substance to be detected, as mentioned in "Advances in X-Ray Analysis", Vol. 9, p. 497 (1967). In this case, it is in usual practice to provide a soller slit between the sample and crystal to let parallel X-rays be incident on the slit. Thus, in order to make effective use of X-rays having passed through the slit it is necessary to select the length l of the crystal to be above $h/\sin \theta$ where h is the aperture height of the soller slit and $\theta$ is the angle of incidence of X-rays on the analysing crystal. If the incidence angle $\theta$ is too small, however, the crystal length l is extremely great, leading to reduction of radiation dose incident on the detector due to scattering in directions normal to the diffraction surface. Therefore, the efficiency of the spectroscope is reduced and too low to be able to make high precision analysis, and the device itself is liable to be extremely large in size. These drawbacks also apply in case of making ultra soft X-ray analysis by using total reflection mirrors.

SUMMARY OF THE INVENTION

An object of the invention, accordingly, is to provide, which is free from the above drawbacks and can make high efficiency analysis in the case where the angle of incidence of X-rays on the analysing crystal or total reflection mirror is small by making effective use of X-rays having passed through the soller slit and also avoiding loss of X-rays due to divergence in directions normal to the diffracting surface.

The invention features an X-ray spectroscope, which comprises a means for causing emission of characteristic X-rays of a sample to be analyzed, a soller slit disposed such that one end thereof faces the sample, a plurality of reflecting means disposed parallel to one another and with one end thereof facing the other end of the soller slit such that X-rays having passed through the soller slit are incident on the reflecting means with a predetermined angle of incidence and a detector, on which the X-rays diffracted by the reflecting means are incident.

Further objects, advantages and features of the present invention will become more fully apparent from a detailed consideration of the arrangement and construction of the constituent parts as set forth in the following specification taken together with the accompanying drawings.

DETAILED DESCRIPTION OF THE PREFERRED EMBODIMENTS

Figure 1:
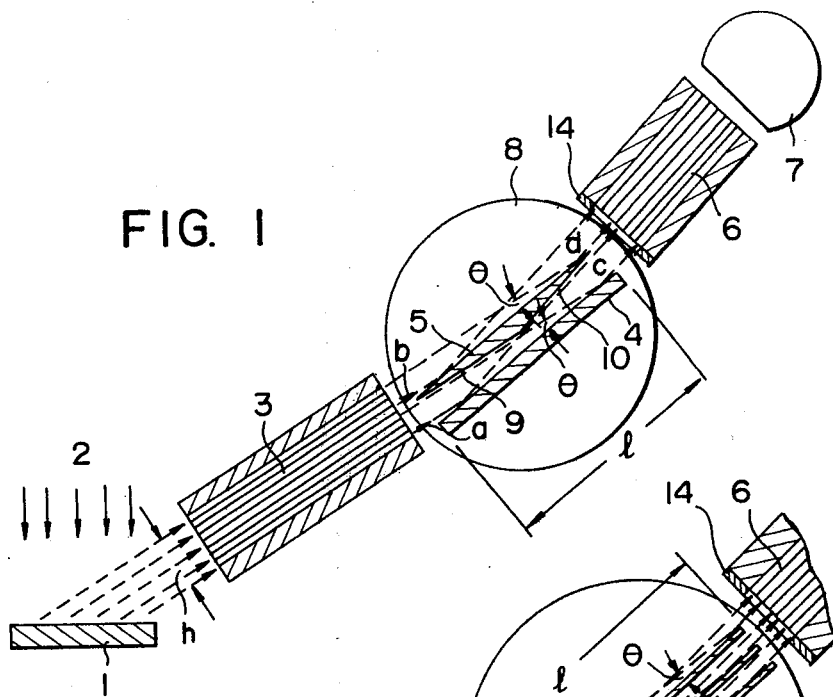
FIG. 1 is a longitudinal sectional view of an embodiment of the invention.

Referring now to FIG. 1, which is a longitudinal sectional view of an embodiment of the invention using analysing crystals, a sample 1 of fluorescent X-ray analysis is irradiated with X-rays 2 from an X-ray tube to cause emission of characteristic X-rays of substances contained in the sample. A divergence soller slit 3 is disposed such that its one end faces the X-ray emitting portion of the sample.

The soller slit 3 comprises a number of parallel plates arranged at a small interval. Two parallel analysing crystals 4 and 5 are disposed such that they face at their one end to the other end of the soller slit 3 and that X-rays a and b having passed through the slit 3 are incident on them with a predetermined diffraction angle $\theta$. A receiving soller slit 6 is disposed such that its one end faces the other end of the analysing crystals 4 and 5, and an X-ray detector 7 is disposed to face the other end of the soller slit 6. The X-rays c and d having been diffracted by the crystals are led through the slit 6 to be incident on the detector 7. In the detector 7, the X-rays are converted into an electric signal and stored in a scaler circuit. The analysing crystals 4 and 5 are mounted on a crystal exchanger 8, so that suitable crystals may be provided between the soller slits 3 and 6 depending upon the spectrum to be detected.

The analysing crystal 5 has a convex back side defined by inclined surfaces 9 and 10 respectively parallel to the X-rays a incident on the crystal 4 and to the X-rays reflected by it, and this back side faces the reflecting surface of the adjacent crystal 4. Thus, it is possible to eliminate or at least reduce loss of part of X-rays having passed through the soller slit 3 due to impingement against the edge of the analysing crystal 5.

In case of using the above device for the measurement of the plating thickness of a tin-coated steel plate through quantitative analysis of tin, for instance, LiF (200) is used as the analysing crystals 4 and 5, with the angle of incidence of X-rays set to 7.01 degrees. Thus, with a crystal length l of, for instance, 75 mm, by setting the aperture height h of the soller slit 3 to about 19 mm practically the entire dose of X-rays having passed through the slit can be made to be incident on the crystals 4 and 5 by one half for each, so that effective analysis of the characteristic X-rays of tin can be obtained.

If it is intended to let practically the entire dose of X-rays having passed through the soller slit with the aperture height of 19 mm as mentioned to be incident on a single analysing crystal, a crystal with the length l of about 150 mm is required from the relation of $l = h/\sin \theta$, leading to scattering in directions normal to the plane of paper of FIG. 1 as mentioned above so that X-radiation incident on the detector 7 is extremely reduced. With the construction of FIG. 1, which uses the two analysing crystals 4 and 5, the crystal length l can be reduced to one half, that is, to 75 mm. Thus, loss of X-rays due to scattering in directions normal to the plane of paper of FIG. 1 can be extremely reduced to improve the reflectivity, and also it is possible to reduce size of the device.

Figure 2:
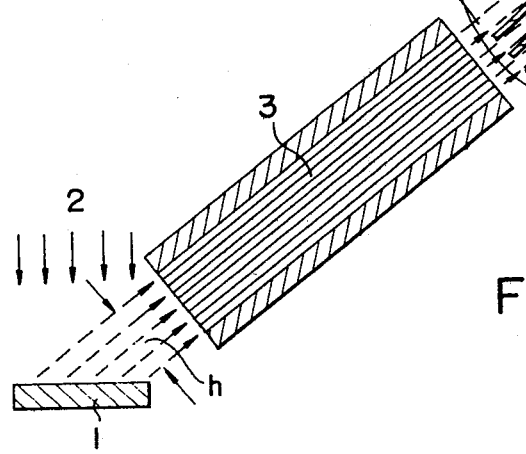
FIG. 2 is a longitudinal sectional view of another embodiment of the invention.

FIG. 2 shows a different embodiment of the invention, which uses total reflection mirrors. More particularly, three parallel total reflection mirrors 11, 12 and 13 are mounted on crystal exchanger 8 disposed between soller slits 3 and 6 such that X-rays having passed through the slit 3 are incident on each mirror with a desired angle of incidence. The mirrors 11, 12 and 13 are each formed by finishing a single crystal silicon wafer such that it has a thickness of about 0.1 mm. Since they are very thin, loss of X-rays due to impingement against their edges can be ignored.

The spectroscope of this embodiment can be used, for instance, for the analysis of boron and carbon contained in a steel sample. Hitherto, metal salts of higher fatty acids have been used as the analysing crystal for the analysis of X-rays of long wavelengths such as the characteristic X-rays of carbon. However, since their reflectivity is very low, namely no higher than several percent, difficulties are encountered in the analysis.

With the total reflection mirrors it is readily possible to obtain high reflectivity of the order of 80 percent. In addition, since almost no elements lighter than carbon are usually contained in the steel sample, it is possible in effect to let only the characteristic X-rays to be reflected and separated by setting the angle $\theta$ of incidence of X-rays on the mirrors to a value slightly below 6.53 degrees, which is the critical angle of $K\alpha$ radiation of carbon with respect to silicon, for instance 6 degrees. When the sample 1 is an alloy, a filter 14, which is capable of absorbing the characteristic X-rays of particular substances and permitting only the X-rays of the relevant substance to be incident on the detector, may be provided either ahead of or behind the receiving soller slit 6.

However, the incidence angle is very small as mentioned above, an intent of permitting practically the total dose of X-rays having passed through the soller slit 3 with a height h of, for instance, 20 mm to be incident on a single mirror requires a very long mirror, that is, with a length l given as $h/\sin\theta$ of 191 mm.

This means that not only the size of the device is extremely increased but also the efficiency of the spectroscope is extremely reduced due to divergence in directions normal to the plane of paper of FIG. 2. With the construction of FIG. 2, which uses the three total reflection mirrors 11, 12 and 13, the length can be reduced roughly to one-third, that is, to 64 mm. Thus, loss of X-rays due to divergence in the directions normal to the plane of paper of FIG. 2 can be extremely reduced to permit 20 times or more the output of analysis in case of the conventional analysing crystals to be obtained, and also it is possible to reduce size of the spectroscope. In other words, according to the invention analysis of carbon contained in steel, which has hitherto been very difficult, can be made readily and accurately.

While the present invention has been described with reference to particular embodiments thereof, it will be understood that numerous modifications may be made by those skilled in the art without actually departing from the spirit and scope of the invention as defined in the appended claims.

What we claim is:

1. An X-ray spectroscope comprising a means for causing emission of characteristic X-rays of a sample to be analyzed, a soller slit disposed such that one end thereof faces said sample, a plurality of reflecting means disposed parallel to one another and with one end thereof facing the other end of said soller slit such that X-rays having passed through said soller slit are incident on said reflecting means with a predetermined angle of incidence and a detector, X-rays diffracted by said reflecting means being incident on said detector.

2. The X-ray spectroscope according to claim 1, wherein said reflecting means each comprise an analysing crystal.

3. The X-ray spectroscope according to claim 1, wherein said reflecting means each comprise a thin total reflection mirror.

4. The X-ray spectroscope according to claim 2, wherein LiF (200) is used as said analysing crystal.

5. The X-ray spectroscope according to claim 3, wherein said mirror is formed by finishing a single crystal silicon wafer.

6. The X-ray spectroscope according to claim 1, which further provides a receiving soller slit between said reflecting means and said detector.

7. The X-ray spectroscope according to claim 1, which further provides a filter capable of absorbing characteristic X-rays of a particular substance, said filter being disposed between said reflecting means and said detector.

8. The X-ray spectroscope according to claim 1, wherein said soller slit comprises a number of plates.

9. The X-ray spectroscope according to claim 1, wherein each said reflecting means has a convex back side defined by inclined surfaces respectively parallel to incident and reflected X-rays, said convex back side facing the reflecting surface of the adjacent reflecting means on the back side.

10. The X-ray spectroscope according to claim 1, wherein said reflecting means are mounted on an exchanger member.

* * * * *

UNITED STATES PATENT AND TRADEMARK OFFICE
CERTIFICATE OF CORRECTION

PATENT NO. : 4,256,961

DATED : March 17, 1981

INVENTOR(S) : Takashi Shoji et al

It is certified that error appears in the above-identified patent and that said Letters Patent is hereby corrected as shown below:

On the title page:

In the heading, at [30] please insert PRIORITY INFORMATION

--Japanese Application No. 19113/54 filed February 22, 1979.--

Signed and Sealed this

Fourth Day of October 1983

[SEAL]

Attest:

GERALD J. MOSSINGHOFF

Attesting Officer     Commissioner of Patents and Trademarks